(12) United States Patent
Kutner et al.

(10) Patent No.: US 7,915,241 B2
(45) Date of Patent: Mar. 29, 2011

(54) PREPARATION OF 24 ALKYL ANALOGS OF CHOLECALCIFEROL AND NON-RACEMIC COMPOUNDS

(75) Inventors: Andrzej Kutner, Warsaw (PL); Jacek Martynow, Warsaw (PL); Michal Chodynski, Pruszkow (PL); Wieslaw Szelejewski, Warsaw (PL); Hanna Fitek, Warsaw (PL); Malgorzata Krupa, Warsaw (PL)

(73) Assignee: Instytut Farmaceutyczny, Warsaw (PL)

( * ) Notice: Subject to any disclaimer, the term of this patent is extended or adjusted under 35 U.S.C. 154(b) by 1412 days.

(21) Appl. No.: 10/962,873

(22) Filed: Oct. 8, 2004

(65) Prior Publication Data

US 2005/0119241 A1    Jun. 2, 2005

(51) Int. Cl.
*A61K 31/56* (2006.01)
*C07C 401/00* (2006.01)

(52) U.S. Cl. ........................ 514/167; 552/653
(58) Field of Classification Search .................. 514/167; 552/653

See application file for complete search history.

(56) References Cited

FOREIGN PATENT DOCUMENTS

| EP | 93305347.2 | 7/1993 |
|---|---|---|
| EP | 0578494 | 6/1995 |
| WO | PCT/DK86/00081 | 7/1986 |
| WO | WO 8700834 | 2/1987 |
| WO | PCT/PL98/00051 | 12/1998 |
| WO | WO 9936400 | 7/1999 |
| WO | PCT/PL03/00037 | 4/2003 |
| WO | WO 03/087048 A2 | 10/2003 |

*Primary Examiner* — Sabiha Qazi
(74) *Attorney, Agent, or Firm* — Husch Blackwell Welsh Katz

(57) ABSTRACT

Disclosed is a process for the preparation of 24-alkyl analogs of cholecalcyferol of Formula 1 having a (5E) or (5Z) configuration, wherein X represents a hydrogen atom, a hydroxy group or an $OR_1$ group, where $R_1$, $R_2$ and $R_3$ may be the same or different and represent groups suitable for hydroxyl protection, and $R_4$ is a $C_{1-6}$ alkyl chain or a $C_{1-6}$ cykloalkyl group, optionally substituted with $C_{1-3}$ alkyl groups, especially for calcipotriol.

The invention also provides new intermediates and non-racemic compounds being valuable synthones for the synthesis of pharmacologically active substances.

6 Claims, 3 Drawing Sheets

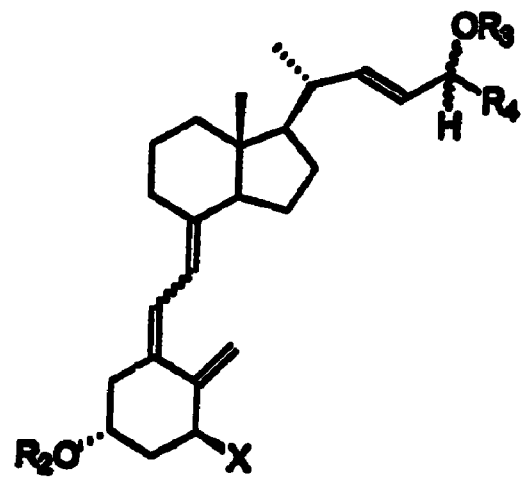
Fig. 1
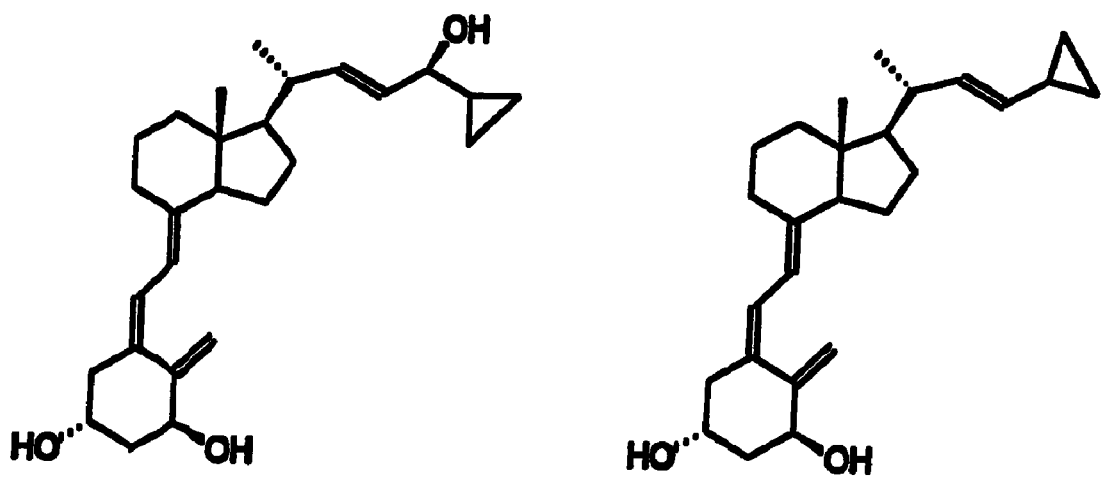
calcipotriol                8
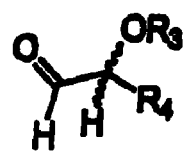
6

SCHEME 1

SCHEME 2

PREPARATION OF 24 ALKYL ANALOGS OF CHOLECALCIFEROL AND NON-RACEMIC COMPOUNDS

CROSS REFERENCES TO RELATED APPLICATIONS

This application is based upon priority International PCT Patent Application No. PCT/PL03/00037, filed Apr. 10, 2003, International Publication No. WO 03/087048 A2, published Oct. 23, 2003, which is based upon priority Polish Application No. 35328 filed Apr. 11, 2002 and priority Polish Application No. 35382 filed May 12, 2002.

BACKGROUND OF THE INVENTION

The invention relates to the preparation of 24-alkyl analogs of cholecalciferol, new intermediates and new non-racemic compounds being valuable synthones for the synthesis of pharmacologically active substances.

In particular the invention relates to the preparation of synthetic analog of vitamin $D_3$-calcipotriol, biologically active compound used in medical treatment.

Calcipotriol, ie. $1\alpha,3\beta,5Z,7E,22E,24S$)-24-cyclopropyl-9,10-secochola-5,7,10(19),22-tetraene-1,3,24-triol, alike natural metabolits of vitamin $D_3$, such as $1\alpha$,24R-dihydroxycholecalciferol (tacalcitol) and 1,25-dihydroxycholecalciferol (calcitriol), exhibits activity inhibiting undesirable proliferation of epidermal keratinocites [F. A. C. M. Castelijins, M. J. Gerritsen, I. M. J. J. van Vlijmen-Willems, P. J. van Erp, P. C. M. van de Kerkhof; *Acta Derm. Venereol.* 79, 111 (1999)].

Preparation of calcipotriol has been disclosed in an International Patent Application WO 8700834, as well as in the publication M. J. Calverley, *Tetrahedron* 43, 4609 (1987). The described method relies on adding side chain C(23)-C(27) to a protected C(22)-aldehyde derivative of (5E)-cholecalciferol, in a Wittig type reaction with (cyclopropyl)carbonylmethylene triphenylphosphate. The C(24)-ketone group is then reduced, giving a mixture of C(24)-epimeric alcohols, which are separated by chromatography to remove the undesirable isomer (24R). Isomer (5E),(24S) is further subjected to a photoisomerization to give isomer (5Z),(24S). In the last step of the synthesis, the silyl protecting groups at C(1)-OH and C(3)-OH are removed to give calcipotriol. Similarly, photoisomerization and deprotection of hydroxyl of the isomer (5E),(24R) gives the (24R)-analog of calcypotriol.

A different method for preparation of calcipotriol (M. J. Calverley, *Synlett* 157, 1990) consists in condensing protected C(22)-diseleneacetal, a derivative of (5E)-cholecalciferol, with (S)-2-[(t-butyl)dimethyl]silyloxy-2-cyclopropylacetate aldehyde. A mixture of diastereoisomeric 23-hydroxy-22-methylselenide thus obtained is treated with methanesulfonic chloride in the presence of triethylamine, to give a compound of the proper configuration (24S), being however a mixture of (22E) and (22Z) olefins. The mixture of (5E),(22E/Z) olefins requires further chromatographic separation and a photoisomerisation to give the compound of (5Z),(22E) configuration. After removing of silyl groups at C(1), C(3) and C(24), calcipotriol is obtained.

Yet another method for preparation of a mixture of C924)-epimers of calcipotriol, described in the Japanese Patent Application JP 08325226 A2, includes coupling of ring A of calcipotriol, that is (4R,6S)-4,6-di(t-butyl)dimethylsilyloxy-7-octen-1-yn, with 7-bromo-derivative formed by CD rings of calcipotriol in a Heck-type reaction, followed by deprotection. It is a multi-step and time-consuming process.

The synthesis of the (7Z)-calcipotriol isomer from a substituted cholesta-5,7-diene by a photochemical transformation or a thermal rearrangement is disclosed in Japanese Patent Application JP 06316558 A2.

All mentioned above methods for preparation of alkyl analogues of cholecalciferol exhibit the following disadvantages: a) tendency to isomerization of asymmetric center at C(20) in the C(22)-aldehyde derivatives of cholecalciferol used as the substrates, b) lack of proper stereoselectivity at the step of C(24)-ketone reduction, c) a need for repeated chromatography, d) use of very unstable derivative of toxic methylselenol, e) lack of stereoselectivity at the step of removing selenium from (-hydroxy)methylselenides, and/or f) the use of difficult to obtain CD ring synthon of calcipotriol. All these factors constitute a serious limitation of the practical value of these methods.

Thus, a new method of synthesis of biologically active 24-alkyl analogs of vitamin D had to be developed that would be effective, short and convenient, making use of available vitamin D derivatives and not requiring the use of very toxic reagents.

BRIEF SUMMARY OF THE INVENTION

The invention provides the method for preparation of 24-alkyl analogs of cholecalciferol of Formula 1 having a (5E) or (5Z) configuration, where X represents a hydrogen atom, hydroxy group or an $OR_1$ group; $R_1$, $R_2$ and $R_3$ may be the same or different and represent a group suitable for hydroxyl protection, and $R_4$ is alkyl or $C_{1-6}$ cycloalkyl group, optionally substituted with $C_{1-3}$ alkyl groups.

The method of the invention comprises the steps of:

(a) reacting a sulfone of Formula 5, possessing a (5E) or (5Z) configuration, wherein the groups X and $R_2$ are defined as above for Formula 1 and $R_5$ is an aryl group or a heterocyclic group comprising at least one heteroatom selected from among oxygen, nitrogen, phosphorus and sulfur, with an aldehyde of Formula 6, having an (R) or an (S) configuration at the carbon atom directly attached to the carbonyl group, wherein $R_3$ is a hydrogen atom or a group suitable for hydroxyl protection and $R_4$ is as defined above for Formula 1, in the presence of a strong base, in an aprotic solvent, and (b) optionally, in case the product has a (5E) configuration, carrying out a photoisomerization reaction of the product obtained as above to a compound of a (5Z) configuration, and (c) removing the protective groups, simultaneously or one after another, from the product possessing the desired configuration at the C(5)-C(6) double bond.

In a preferred embodiment, the invention provides the method for preparation of 24-alkyl analog of cholecalciferol of Formula 1, where X is the hydroxy group; $R_1$, $R_2$ and $R_3$ are hydrogen atoms, and $R_4$ is a cyclopropyl group, ie. calcipotriol.

The invention further provides the method for preparation of non-racemic enantiomerically enriched cyclopropane synthones of Formula 6, in which: $R_3$ is H, a protecting acyl, ether, alkoxy or —$SiR_8R_9R_{10}$ group, wherein $R_8$-$R_{10}$ are the same or different and represent phenyl or alkyl $C_1$-$C_4$, and $R_4$ is a $C_{1-6}$ alkyl or a $C_{1-6}$ cykloalkyl, optionally substituted with $C_{1-3}$ alkyl groups. The enantiomerically enriched compounds of Formula 6 are the substrates for the 24-alkyl analogs of cholecalciferol.

The invention also provides new sulfones of Formula 5 possessing a (5E) or a (5Z) configuration, wherein X is a hydrogen atom, a hydroxy group or an $OR_1$ group, where $R_1$ and $R_2$ are the same or different and are groups suitable for hydroxyl protection, and $R_5$ is a heterocyclic group comprising at least one heteroatom selected from among oxygen, nitrogen, phosphorus and sulfur. Sulfones of Formula 5 are used as substrates in the process for preparation of the 24-alkyl analogs of cholecalciferol.

The invention also provides the method for preparation of the sulfones of Formula 5, possessing a (5E) or a (5Z) configuration, wherein X is a hydrogen atom, a hydroxy group or an $OR_1$ group, where $R_1$ and $R_2$ are the same or different and are groups suitable for hydroxyl protection, and $R_5$ is a heterocyclic group comprising at least one heteroatom selected from among oxygen, nitrogen, phosphorus and sulfur, said method comprising reacting a derivative of 22-hydroxy cholecalciferol of Formula 3, having a (5E) or a (5Z) configuration, where X is a hydrogen atom, a hydroxy group or an $OR_1$ group where the groups $R_1$ and $R_2$ are the same or different and represent groups suitable for hydroxyl protection, with a thiol of the Formula: $R_5$—SH, wherein $R_5$ is defined as above for Formula 5, followed by a selective oxidation of the thus obtained sulfide of Formula 4.

The invention further provides new sulfides of Formula 4 of configuration (5E) or (5Z), where X is hydrogen, hydroxyl or $OR_1$ group, $R_1$ and $R_2$ may be the same or different and represent hydroxyl protecting group, where the groups $R_1$ and $R_2$ are the same or different and represent groups suitable for hydroxyl protection, and $R_5$ is a heterocyclic group comprising at least one heteroatom selected from among oxygen, nitrogen, phosphorus and sulfur. Sulfides of Formula 4 are isolated as intermediates in the process for preparation of the 24-alkyl analogs of cholecalciferol.

A more detailed description of the invention is provided in the following description and appended claims taken in conjunction with the accompanying drawings.

BRIEF DESCRIPTION OF THE DRAWINGS

FIG. 1 shows the 24-alkyl analogs of cholecalciferol of Formula 1 prepared by the method of the invention as well as compounds of Formula 6 being the substrates for the synthesis.

DETAILED DESCRIPTION OF THE INVENTION

Figure 2:
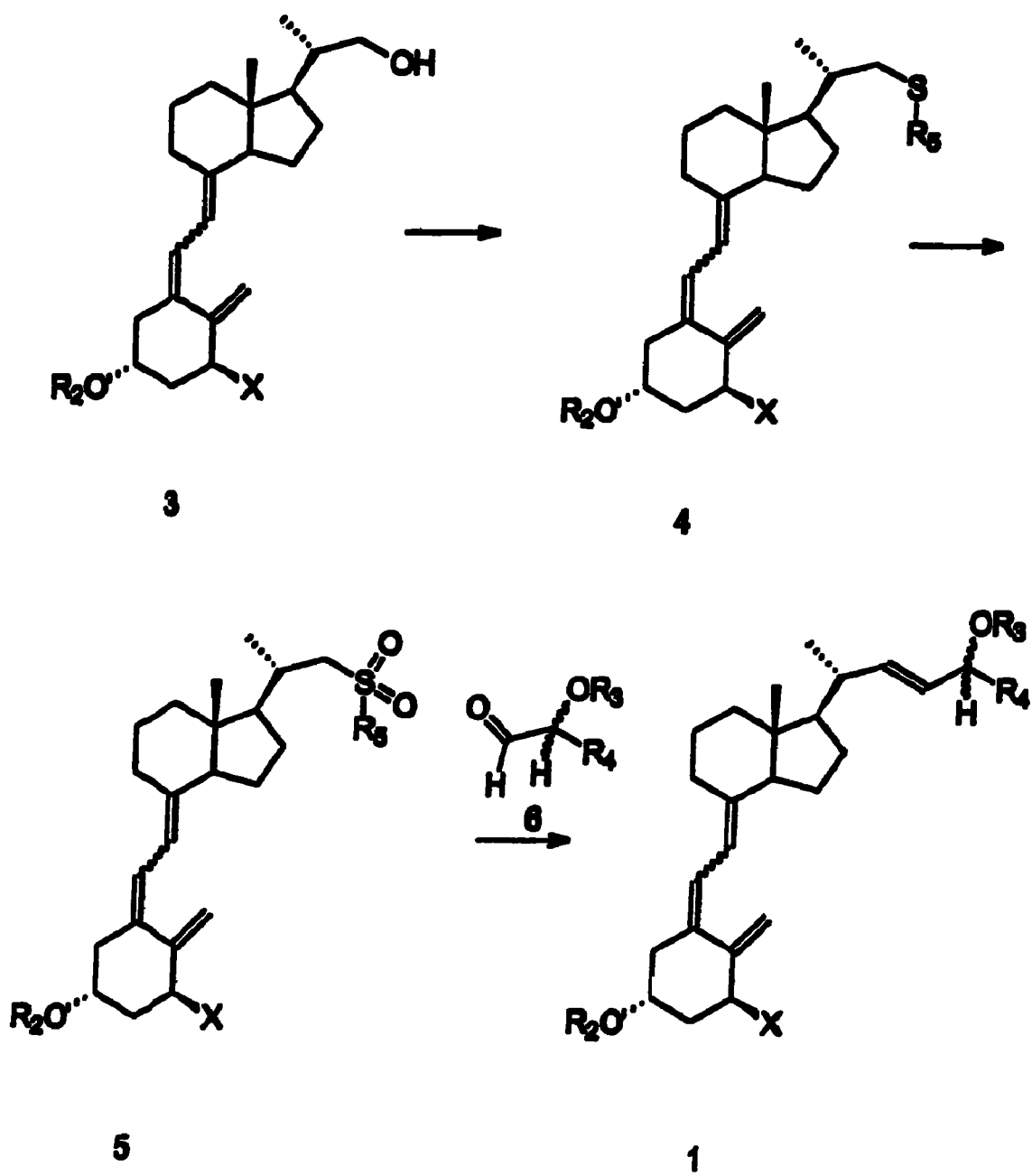
FIG. 2 represents the Scheme of synthesis of 24-alkyl analogs of cholecalciferol of Formula 1 by the method of the invention.
Figure 3:
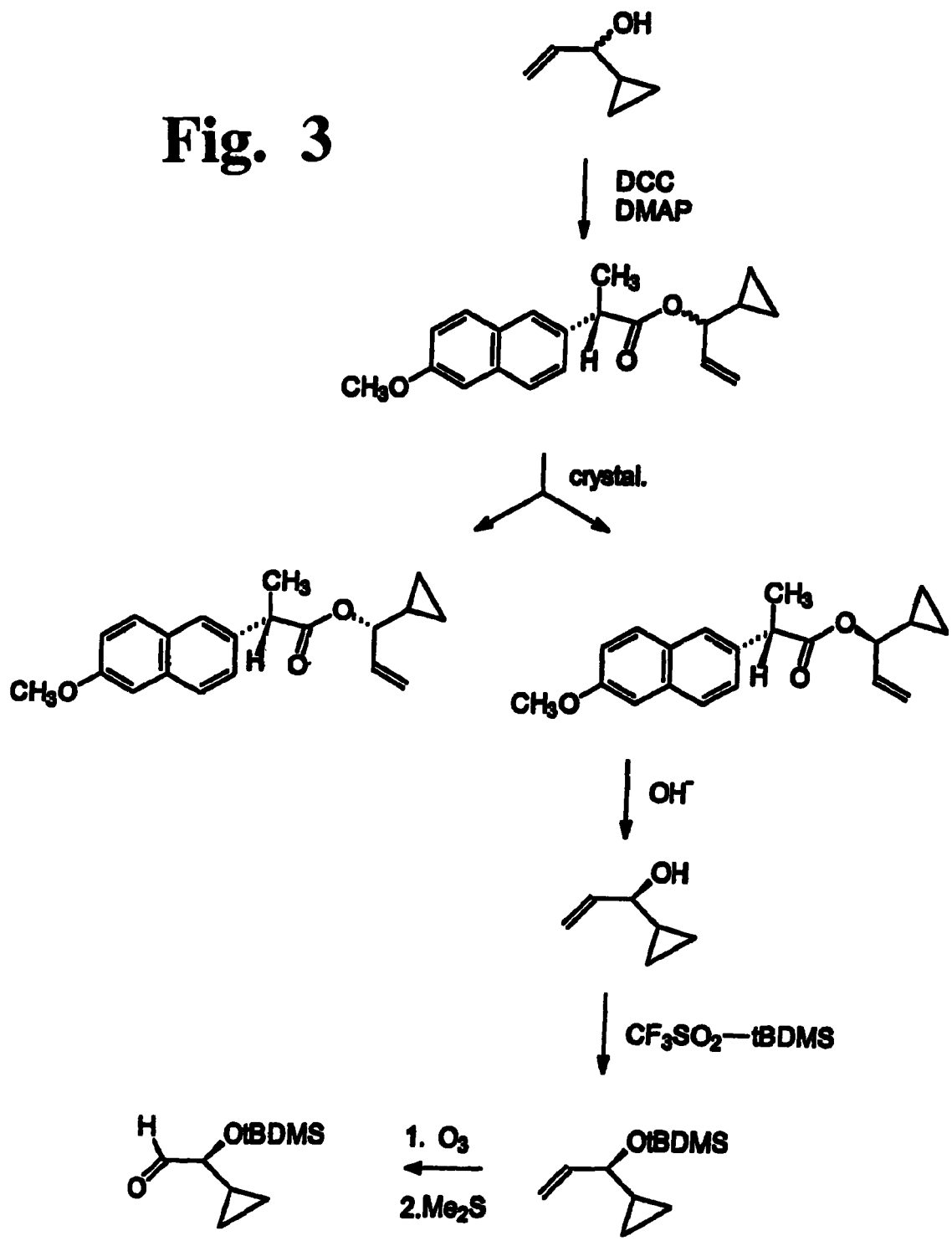
FIG. 3 represents the Scheme of the synthesis of compound of Formula 6, wherein $R_3$=t-butyldimethylsilyl and $R_4$=cyclopropane.

The following is a detailed description and explanation of the preferred embodiments and best modes for embodying the invention along with some examples thereof.

The method for preparation of 24-alkyl analogs of cholecalciferol of Formula 1 having a (5E) or (5Z) configuration, where X represents a hydrogen atom, hydroxy group or an $OR_1$ group, $R_1$, $R_2$ and $R_3$ may be the same and represent a group protecting the hydroxy group, and $R_4$ is a alkyl chain or a $C_{1-6}$ cycloalkil group, optionally substituted with $C_{1-3}$ alkyl groups, comprises reacting a sulfone of Formula 5, possessing a (5E) or (5Z) configuration, wherein the groups X and $R_2$ are defined as above for Formula 1 and $R_5$ is an aryl group or a heterocyclic group comprising at least one heteroatom selected from oxygen, nitrogen, phosphorus and sulfur, with an aldehyde of Formula 6, having an (R) or an (S) configuration at the carbon atom directly attached to the carbonyl group, wherein $R_3$ is a hydrogen atom or a group suitable for hydroxyl protection and $R_4$ is as defined above for Formula 1, in the presence of a strong base, in an aprotic solvent. Optionally, in case the product has a (5E) configuration, the process involves carrying out a photoisomerization reaction of the product obtained as above to a compound of a (5Z) configuration and then removing the protective groups, simultaneously or one after another, from the product possessing the desired configuration at the C(5)-C(6) double bond.

Hydroxyl protecting group may be any group used in vitamin D chemistry to protect hydroxyl groups, such as for example acyl, alkylsilyl or alkoxyalkyl. As alkylsilyl protecting groups can be mentioned trimethylsilyl, triethylsilyl or t-butyldimethylsilyl group. Typical alkoxyalkyl groups are methoxymethyl, etoxymethyl, tetrahydrofuranyl and tetrahydropyranyl.

Protecting groups may be removed from the obtained product of a desired configuration simultaneously, with e.g. tetrabutylammonium fluoride or removing of protecting groups may be carried out in two or three steps, giving mono- or di-protected cholecalciferol analogs, respectively.

In case sulfone having (5Z) configuration is used as a substrate, a product of Formula 1 of (5Z) configuration is obtained. In case sulfone having (5E) configuration is used, a product of Formula 1 having (5E) configuration is obtained, which may further be photoisomerised to compound having desired (5Z) configuration, e.g. according to the method described in WO 8700834.

The method of the invention may be useful for preparation of a number of valuable cholecalciferol derivatives, possesing a double bond and an 24-alkyl group, especially cycloalkyl $C_{3-6}$ group, in the side chain.

In the preferred embodiment, the invention relates to the method for preparation of calcipotriol of Formula 1a, wherein X is a hydroxyl group, $R_1$, $R_2$ and $R_3$ are the same hydroxyl groups, and $R_4$ is cyclopropyl, having (5Z) configuration. In case calcipotriol is obtained, sulfone of Formula 5, where X is $OR_1$ group, $R_1$, $R_2$ and $R_3$ are protective groups, and $R_5$ is aryl or heterocyclic group, is reacted with aldehyde of Formula 6, in which $R_3$ is hydrogen or a protective group, and $R_4$ is cyclopropyl, especially with (R)- or (S)-2-[(t-butyl)dimethyl] silyloxy-2-cyclopropylacetaldehyde.

In sulfones of Formula 5, $R_5$ may be an aryl group, such as phenyl, e.g. 4-methylphenyl, 1-naphthyl, 2-naphthyl, or heterocyclic group, e.g. 2-thiazole, 2-benzothiazole, 1-phenyl-1H-tetrazol-5-yl, 2-pirydyl, 2-pirymidynyl, 1-isochinolinyl, 1-methyl-2-imidazolil, 4-alkyl-1,2,4-triazol-3-yl or other heterocyclic group.

Some sulfones of Formula 5, wherein $R_5$ is phenyl group or substituted phenyl group, are known in the art as the key synthons used in vitamin D chemistry, e.g. for obtaining 24- or 25-hydroxy-derivatives of cholecalciferol. However, substituting a carbon atom of a sulfone group by phenyl causes, in case of some cholecalciferol derivative synthesis, the need for reducing C(22)-sulfonyl group after condensation, with e.g. sodium amalgam.

It has been unexpectedly found that the presence in the sulfone of Formula 5 of activating heterocyclic group $R_5$ containing at least one of the heteroatoms as oxygen, nitrogen, phosphor or sulfur, attached to the carbon atom adjacent to sulfone group, makes possible omitting the step of desulfonation, due to the fact that sulfone group together with heterocyclic group are easily removed during condensation of sulfone with aldehyde.

Sulfones of (5E) or (5Z) configuration of Formula 5, where X is hydrogen atom, hydroxyl or $OR_1$ group, $R_1$ and $R_2$ may be the same or different and represent hydroxyl protective group, and $R_5$ is heterocyclic group containing at least one of the following atoms: oxygen, nitrogen, phosphorous and sulfur, are novel compounds.

New sulfones of Formula 5 may be used for obtaining other analogues of cholecalciferol of shorter side chain, such as for ble a new compound (5Z,7E,22E)-(1S,3R)-1,3-dihydroxy-23-cyclopropyl-24-nor-9,10-secochola-5,7,10(19),22-tetraen of Formula 8.

Sulfones of (5E) or (5Z) configuration depicted by Formula 5 according to the invention are obtained from 22-hydroxy derivatives of cholecalciferol of (5E) or (5Z) configuration of Formula 3, where X is hydrogen, hydroxyl or $OR_1$ group, $R_1$ and $R_2$ may be the same or different and represent hydroxyl protective group, in the Mitsunobu reaction with thiol $R_5$—SH, where $R_5$ is as described for Formula 5. Then, the obtained sulfides of Formula 4 are selectively oxidized.

Selective oxidation may be carried out with the oxidizing reagents such as organic peracids, especially m-chloroperbenzoic acid or magnesium monoperphthalate, hydrogen peroxide, Oxone® (mixture of 2 $KHSO_5$:$KHSO_4$:$K_2SO_4$), ammonium heptamolybdate-hydrogen peroxide system, tertiary amine(N-methylmorpholine or trialkylamine) N-oxide-tetrapropyloammonium perruthenate system.

Before oxidation, the triene system of sulfide may optionally be protected by forming an adduct with a Diels-Alder reagent, eg. with sulphur dioxide, and then removing the protection after oxidation by the method of thermolysis.

Alternatively, sulfides of Formula 4 may be prepared via intermediate C(22)-hydroxy-sulfonates obtained from compounds of Formula 3, in the reaction of substitution with thioalkoxyl $R_5S^-$ anion, where $R_5$ is as described for Formula 5.

The starting C(22)-hydroxy derivatives of Formula 3 are generally known in vitamin D chemistry and are described for example in U.S. Pat. No. 4,847,012; A. Kutner at all, *Tetrahedron Lett.*, 28, 6129 (1987); A. Kutner at all, *J. Org. Chem.* 53, 3450 (1988).

Sulfides isolated in the method according the invention represented by Formula 4, wherein X is hydrogen, hydroxyl or $OR_1$ group, $R_1$ and $R_2$ may be the same or different and represent hydroxyl protective group, $R_5$ represents aryl or heterocyclic group containing at least one heteroatom selected from among oxygen, nitrogen, phosphorous and sulfur, are novel compounds.

The method for preparation of 24-alkyl derivatives of cholecalcyferol of Formula 1 is as follows.

From the starting sulfone [(5E) or (5Z) configuration, of Formula 5, where X is $OR_1$ group, $R_1$, $R_2$ and $R_3$ are protective groups, and $R_5$ is aryl or heterocyclic group, C(22)-carbanion is generated with the use of strong organic base. The proper bases to apply are alkyllithium, alkylsodium, alkylpotassium, alkali metal amide or N-substituted alkali metal, in particular potassium, sodium or lithium N,N-bis(trimethylsilyl)amide.

The reaction of condensation of carbanion of sulfone of Formula 5 with non-racemic compounds of Formula 6 is preferably carried out in aprotic solvent, selected from a group of hydrocarbons or ethers, especially in 1,2-dimethoxyethane or tetrahydrofuran.

Enantiomerically pure or enatiomerically enriched compounds of Formula 6, having synthone's side chain structure of final compound of Formula 1, constitute mainly substituted derivatives of acetaldehyde, in which $R_3$ group represents e.g. alkylsilyl group, alkyl(aryl)silyl group, 1-alkoxyalkyl or 2-alkoxyalkyl group.

The non-racemic compounds of Formula 6, in which $R_3$ is H, a protecting acyl, ether, alkoxy or —$SiR_6R_7R_8$ group, wherein, $R_6$-$R_8$ are the same or different and stand for a phenyl:

(a) addition of a vinylmagnesium halide to a cyclopropanecarboxylic aldehyde to form a racemic allyl alcohol, (b) esteryfication of the allyl alcohol with an enantiomerically pure acid R*—COOH, wherein R* is a chiral substituent possessing the center of assymetry in the position directly adjacent to the carboxy group, (c) separation of diastereoisomeric esters to optically pure or highly diastereoisomerically enriched diastereoisomers, (d) hydrolysis of the above formed ester to form enantiomerically pure or enantiomerically enriched alcohol or its epimer, and then optionally protecting the hydroxyl group as $R_3$, (e) oxidative cleavage of the double bond.

The organic eneantiomerically pure acids R*—COOH used in the step (b) are, but are not limited to, (2S)-2-(6'-methoxy-2'-naphthyl)propionic acid, 2-O,3-O-dialkyl-, 2-O,3-O-diaryl- or 2-O,3-O-diacyl-derivatives of D-tartaric or L-tartaric acid, 2-O-aryl-, 2-O-acyl- or 2-O-alkyl-derivatives of lactic acid, (−)-N-acetylleucine, (R)-(−)-$C_6H_5$CH($OCH_3$) $CO_2H$, (S)-(+)-$C_6H_5$CH($OCH_3$)$CO_2H$, (R)-(−)-$C_6H_5$CH(OAc)$CO_2H$ and (S)-(+)-$C_6H_5$CH(OAc)$CO_2H$. The other optically active organic acids applicable for the resolution of racemic alcohols are obvious to those skilled in the art.

In case (2S)-2-[(t-butyl)dimethyl]silyloxy-2-cyclopropylacetaldehyde is prepared, racemic or partially racemic 3-cyclopropyl-3-hydroxy-1-propen is esterified with optically active (S)-(+)-(6-methoxy-α-methyl-2-naphtalene)propionic acid (naproxen) and the thus formed diastereoisomeric esters are separated by fractional crystallization. In the next step, the ester group of the thus obtained crystalline, optically pure or highly diastereomerically enriched isomer of 3"-cyclopropyl-1"-propen-3"-yl(2S/3"R)-2-(6'-methoxy-2'-naphthyl) propionate is hydrolyzed, then the hydroxy group is silylated, followed by ozonolysis of the double bond present in the thus formed (3R)-3-cyclopropyl-3-hydroxy-1-propene, affording (2S)-2-[(t-butyl)dimethyl]silyloxy-2-cyclopropylacetaldehyde with a very high enantiomeric excess.

Non-racemic synthones obtained according to the method of the invention possess an enatiomeric excess of one of the isomers of absolut configuration (R) or (S), wherein an enantiomeric excess "ee" is denominated, according to the definition in J. March, Advanced Organic Chemistry; Reactions, Mechanisms, and Structure, IV ed., Ed. J. Wiley&Sons, p. 125, as an excess of more than 50%.

An alternative method for preparation of non-racemic cyclopropane synthones of formula 6 consists in oxidation of proper sulfonates or alkyl halides with dialkylsulfoxides, especially with dimethylsulfoxide (Kornblum type reaction). Oxidation under these conditions is not accompanied with racemisation of the assymetric center adjacent to the carbonyl group in the resulting aldehyde.

The methods according to the present invention as well as the enantiomerically enriched synthones described herein make possible a convenient and effective rout for preparing of biologically active substances, especially 24-alkyl analogs of vitamin D, possessing a C(22)-C(23) unsaturated bond, from readily available vitamin intermediates, in a few steps, excluding the use of toxic or noxious reagents or the risk of epimerization. Tedious separations and troublesome reductions of the 23-hydroxy-22-sulfone intermediates, known in the art of vitamin D analogs synthesis, are thus avoided.

EXAMPLE 1

The method for preparation of 24-alkyl cholecalciferol derivatives of the invention is characterized by high stereo- and regioselectivity. The C(22),C(23)-unsaturated product is obtained with the proper (22E) configuration, which is preferred due to the biological activity and the simplicity of isolation. Depending on the configuration of the starting aldehyde, the product has a defined configuration at the C(24) carbon. Moreover, the (5E) isomer can be converted by known methods into the pharmaceutically preferred (5Z) isomer. t-Butyl)dimethyl]silyloxy-2-cyclopropyl-acetaldehyde
a) (1S)-1-[(t-Butyl)dimethyl]silyloxy-1-cyclopropyl-2-(4-toluenesulfonyloxy)ethane (ee=64%; 870 mg, 2.35 mmole) was dissolved in anhydrous dimethylsulfoxide (Aldrich, 15 mL). 2,4,6-Trimethylpiridyne (1.25 mL, 1.14 g, 9.4 mmole) was added and the mixture was stirred/$N_2$. The flask with reaction mixture was placed on an oil-bath at 150° C. and the stirring was continued/$N_2$ for 2 h. Then the reaction mixture was cooled to room temp., poured into $H_2O$ (100 mL) and extracted with diisopropyl ether (60 mL). The phases were separated, the water phase was extracted again with diisopropyl ether (30 mL). The combined organic phases were washed with 10% aq. $KHCO_3$ (80 mL), dried over anhydrous $Na_2SO_4$ (20 g). The drying agent was filtered off and washed with diisopropyl ether (20 mL). The combined filtrates were concentrated in vacuo (10 mm Hg, bath temp. 0° C.). The crude product was purified on the column with silica gel (230-400 m, 40 g, 15% $CH_2Cl_2$/hexane). (2S)-2-[(t-Butyl)dimethyl]silyloxy-2-cyclopropylacetaldehyde was obtained as a colourless, labile oil (250 mg, 50%); $C_{11}H_{22}O_2Si$; $[\alpha]_D=(-)31°$ (20° C., c=1, $CHCl_3$); $^1$H-NMR (500 MHz, $CDCl_3$) δ 9.58 (1H, d: 2.2 Hz), 3.58 (1H, dd: 6.4, 2.2 Hz), 1.01 (1H, m), 0.91 (9H, s), 0.52 (2H, m), 0.43 (2H, m), 0.07 (3H, s) and 0.06 (3H,s) ppm; $^{13}$C-NMR (50 MHz, $CDCl_3$) δ 202.5, 79.4, 25.7 (3×C), 18.2, 12.6, 1.6, 0.6, −4.7 i −4.8 ppm.

b) (1S)-1-[(t-Butyl)dimethyl]silyloxy-1-cyclopropyl-2-(4-toluenesulfonyloxy)ethane (ee=75%; 4.31 g, 11.6 mmole) was oxidized at the conditions described above. After the work-up and chromatography, (2S)-2-[(t-butyl)dimethyl]silyloxy-2-cyclopropylacetaldehyde as a colourless liquid (1.23 g, 49.3%) was obtained; $^1$H-NMR and $^{13}$C-NMR spectra as described in (a); $[\alpha]_D=(-)35.0°$ (20° C., c=1, $CHCl_3$); literature data: Calverley, M. J. *Synlett* 1990, 157: (−)40.4° for the sample of ee=95%. The comparison of $[\alpha]_D$ as determined and literaature $[\alpha]_D$, gave the value ee=82% (S/R>10:1).

EXAMPLE 2

{3R/S)-3-Cyclopropyl-3-hydroxy-1-propene Cyclopropanecarboxyaldehyde (Aldrich, 10.3 g, 11.0 ml, 146.9 mmole) was dissolved in an anhydrous tetrahydrofurane (150 mL). The solution was cooled/$N_2$ do −78° C., and then, while stirring vigorously, 1.0 M vinylmagnesium bromide in THF (185 mL, 185 mmole) was slowly added. After 15 min. the cooling bath was changed for water-ice bath and the stirring was continued at 0° C. for 1 h. Then the saturated brine (10 mL) was slowly added while stirring, and then more brine (100 mL) and hexane (250 mL) were added. The phases were extracted and separated, the organic phase was washed with diluted brine twice, and then dried over anhydrous $K_2CO_3$ (50 g). The drying agent was filtered off and washed with hexane (50 mL). The combined filtrates were concentrated under vacuum (10 mm Hg, 15° C.) and dried under vacuum at the same conditions. A colourless thick oil (13.6 g, 94%) was obtained, homogenous at TLC and NMR. $C_6H_{10}O$; El MS m/z 98 (M+, 2), 80 (16); $^1$H-NMR (500 MHz, $CDCl_3$) δ 5.95 (1H, ddd: 17.2, 10.5,5.8 Hz), 5.26 (1H, dt: 17.2, 1.5 Hz), 5.12 (1H, dt: 10.5, 1.5 Hz), 3.49 (1H, bt: 6.6 Hz), 1.71 (1H, bs, og), 0.99 (1H, m), 0.54 (2H, m), 0.36 (1H, m), 0.27 (1H, m) ppm.

EXAMPLE 3

(3R/S)-3-[(t-Butyl)dimethyl]silyloxy-3-cyclopropyl-1-propene. (3R/S)-3-Cyclopropyl-3-hydroxy-1-propene (3.00 g, 30.56 25 mmole) was dissolved in anhydrous $CH_2Cl_2$ (100 ml). The solution was cooled/$N_2$ to 0° C. $Et_3N$ (4.95 g, 6.82 ml, 48.9 mmol) was added with vigorously stirring. Then t-butyl(dimethyl)silyl-trifluoromethane-sulfonate (Fluka, 9.13 ml, 10.5 g, 39.7 mmole) was slowly added. The stirring was continued at 0° C. for 1 h and 10% aq. $KHCO_3$ (100 ml) was added. The cooling bath was removed and the mixture was stirred for 1 h. $CH_2Cl_2$ (100 ml) was added, the phases were separated and the organic phase was shaken three times with $KHCO_3$ (3×150 mL) and dried over anhydrous $K_2CO_3$. The drying agent was filtered off and washed with $CH_2Cl_2$. The combined filtrates were concentrated and dried under vacuum. The crude product was purified on the column with silica gel (230-400 m, 250 g, 5% EtOAc/hexane). A colourless oil (4.72 g, 73%) yielded, homogenous at TLC and NMR; $C_{12}H_{24}OSi$; El MS m/z 212 (7) and $_1$H-NMR (200 MHz, $CDCl_3$) δ 5.90 (1H, ddd: 16.9, 10.3, 6.2 Hz), 5.18 (1H, bd: 17.2 Hz), 5.03 (1H, bd: 10.3 Hz), 3.65 (1H, bt: 6.2 Hz), 0.90 (9H, s), 0.89 (1H, m), 0.45 (2H, m), 0.30 (2H, m), 0.06 (3H, s), 0.04 (3H, s) ppm.

EXAMPLE 4

(3"R/S)-3"-cyclopropyl-1"-propen-3"-yl (2S)-2-(6'-metoxy-2'-naphtyl)propionate and (3"R)-3"-cyclopropyl-1"-propen-3"-yl (2S)-2-(6'-metoxy-2'-naphtyl)propionate. (3R/S)-3-Cyclopropyl-3-hydroksy-1-propene (7.00 g, 71.3 20 mmole) was dissolved in anhydrous toluene (25 mL). The solution was slowly dropped at room temp./$N_2$ to a vigorously stirred mixture of toluene (100 mL), (S)-(+)-[6-methoxy-α-methyl-2-naphtalene]acetic acid (Aldrich, 19.80 g, 86 mmole), dicyclohexylcarbodiimide (18.36 g, 89 mmole) and 4-(dimethylamine)piridyne (1.05 g, 8.6 mmole). When the alcohol dropping completed, the reaction mixture was warmed to 68° C. After 30 min. stirring, toluene (100 mL) and ethyl acetate (250 mL) were added and the mixture was cooled to room temp. The solid was filtered off and washed with toluene (70 mL). The combined filtrates were extracted with water (2×250 mL), 10% aq. $KHCO_3$ (2×250 mL) and water (2×250 mL). The organic phase was dried over $MgSO_4$ (70 g). The drying agent was filtered off and washed with toluene (50 mL). The combined filtrates were concentrated in vacuo. The crude product was purified on the column with silica gel (230-400 m, 440 g, gradient 4% to 15% EtOAc in hexane). The mixture of diastereoisomers was obtained (3"R/S) as a colourless, solidifying oil (17.56 g, 79%), not separating to diastereoisomers at TLC (EtOAc/hexane); $C_{20}H_{22}O_3$; $[\alpha]_D=+6.5°$ (20° C., c=1, $CHCl_3$); $^1$H-NMR (500 MHz, $CDCl_3$) δ 7.67 (3H, m), 7.41 (1H, m), 7.11 (2H, m), 5.84 (0.5H, ddd: 17.2, 10.5, 5.9 Hz), 5.71 (0.5H, ddd: 17.1, 10.6, 7.6 Hz), 5.24 (0.5H, bd: 17.2 Hz), 5.13 (0.5H, bd: 10.6 Hz), 5.04 (0.5H, bd: 17.3 Hz), 4.99 (0.5H, bd: 10.6 Hz), 4.74 (1H, m), 3.91 (3H, s), 3.89 (1H, 2×q: 7.2 Hz), 1.58 (1.5H, d: 7.2 Hz), 1.575 (1.5H, d: 7.2 Hz), 1.04 (0.5H, m), 0.95 (0.5H, m), 0.52 (1.5H, m), 0.44 (0.5H, m), 0.39 (1H, m), 0.28 (0.5H, m), 0.19 (0.5H, m) ppm. This sample was crystalized 5 times in n-heptane at −10° C. Diastereoisomer (3"R) of an ester was obtained as a crystalline white solid (1.61 g, 9.2%); m.p.=59-60° C.; $[\alpha]_D=+51.5°$ (20° C., c=1, $CHCl_3$); after HPLC (Chiralcel® OD column; 2% isopropanol/hexane), the sample's purity=98%; $^1$H-NMR (500 MHz, $CDCl_3$) δ 7.67 (3H, m), 7.41 (1H, dd: 8.4, 1.8 Hz), 7.12 (2H, m), 5.71 (1H, ddd: 17.2, 10.6,5.6 Hz), 5.04 (1H, dt: 25 17.2, 1.4 Hz), 4.99 (1H, dt: 10.6, 1.2 Hz), 4.72 (1H, bdd: 7.0, 5.7 Hz), 3.91 (3H, s), 3.885 (1H, q: 7.2 Hz), 1.58 (3H, d: 7.2 Hz), 1.04 (1H, m), 0.53 (2H, m), 0.39 (1H, m), 0.29 (1H, m) ppm. The filtrates of crystallisation did not give the other diastereoisomer in a pure form, they were enriched with this one.

EXAMPLE 5

(3R)-3-Cyclopropyl-3-hydroxy-1-propene. (3"R)-3"-Cyclopropyl-1"-propen-3"-yl (2S)-2-(6'-methoxy-2'-naphtyl)propionate (827 mg, 2.66 mmole) was dissolved in tetrahydrofuran (3 mL) and MeOH (15 mL) and $H_2O$ (1 mL) were added. The mixture was stirred/$N_2$ at room temperature and LiOH×$H_2O$ (1.6 g) was added. After 4 h the mixture was poured into $H_2O$ (70 mL), extracted with $CH_2Cl_2$ (3×40 mL). The combined organic phases were dried over anhydrous $MgSO_4$ and concentrated in vacuo (0° C., 10 mm Hg). A colourless oil obtained was purified on silica gel (230-400 mesh, 7 g, 3%-10% EtOAc/hexane). The product was concentrated and dried in vacuo (0° C., 10 mm Hg). (3R)-3-Cyclopropyl-3-hydroxy-1-propene as a colourless oil (171 mg, 65%) was obtained; $C_{12}H_{24}OSi$; E1 MS m/z 212 (6); $[\alpha]_D=+47°$ (20° C., c=1, $CHCl_3$); $^1$H-NMR (200 MHz, $CDCl_3$) as in Example 14 for the racemic compound.

EXAMPLE 6

(3R)-3-t-Butyl(dimethyl)silyloxy-3-cyclopropyl-1-propene. R)-3-Cyclopropyl-3-hydroxy-1-propene (150 mg, 1.53 mmole) was dissolved in anhydrous $CH_2Cl_2$ (5 ml) and the mixture was stirred at 0° C./$N_2$. Then $Et_3N$ (248 mg, 341 μL, 2.45 mmole) and t-butyl(dimethyl)silyl-trifluoromethanesulfonate (525 mg, 456 mL, 1.99 mmol) were added. After 1 h 10% aq. $KHCO_3$ (5 mL) was added and the mixture was stirred at room temp. for 1 h. $CH_2Cl_2$ (5 mL) was added, the phases were separated, the organic phase was washed with 10% aq. $KHCO_3$ solution (3×8 mL). The combined organic phases were dried over anhydrous $K_2CO_3$, filtered and concentrated in vacuo. The crude product was purified on the column with silica gel (230-400 mesh, 10 g, hexane). After drying the product under vacuum (0° C., 10 mm Hg), (3R)-3-t-butyl(dimethyl)silyloxy-3-cyclopropyl-1-propene as a colourless oil (250 mg, 77%) was obtained; $C_{12}H_{24}OSi$; E1 MS m/z 212 (M+, 3%); $[\alpha]_D=+8.0°$ (20° C., c=1, $CHCl_3$); $^1$H-NMR (200 MHz, $CDCl_3$) δ 5.89 (1H, ddd: 16.9, 10.4, 5.6 Hz), 5.16 (1H, ddd: 17.2, 2.0, 1.2 Hz), 5.02 (1H, ddd: 10.4, 1.8, 1.2 Hz), 3.65 (1H, bt: 6.3 Hz), 0.90 (9H, s), 0.89 (1H, m), 0.43 (2H, m), 0.30 (1H, m), 0.26 (1H, m), 0.05 (3H, s), 0.03 (3H, s) ppm.

EXAMPLE 7

(2S)-2-[(t-Butyl)dimethyl]silyloxy-2-cyclopropylacetaldehyde(3R)-3-t-Butyl(dimethyl)silyloxy-3-cyclopropyl-1-propene (150 mg, 0.706 mmole) was dissolved in n-pentane (25 mL). The solution was cooled to −78° and then the stream of oxygen with $O_3$ was introduced until the intensively blue colour appear. Then the solution was blown with the mild stream of oxygen for 10 min., $(CH_3)_2S$ (3 mL) was added and allowed to warm to room temp. for 20 h. The solution was concentrated in vacuo (0° C., 10 mm Hg) to 2 mL volume, and then was chromatographed on the column with silica gel (230-400 mesh, 10 g, 5%-15% $CH_2Cl_2$/hexane). The pure fractions were concentrated and dried in vacuo. (2S)-2-[(t-Butyl)dimethyl]silyloxy-2-cyclopropylacetaldehyde as a colourless oil (53 mg, 35%) was obtained; $[\alpha]_D=(-)34.0°$ (20° C., c=1, $CHCl_3$); $^1$H-NMR (200 MHz, $CDCl_3$). b) (1S)-1-Cyclopropyl-1,2-dihydroxyethane (ee=75%; 2.29 g, 22.4 mmole) was reacted with p-toluenesulfonate chloride according to the procedure of (a). After work-up and chromatography, (1S)-1-cyclopropyl-1-hydroxy-2-(4'-toluenesulfonyloxy)ethane as a colourless, viscous oil (3.48 g, 60.5%) was obtained; $^1$H-NMR and $^{13}$C-NMR spectra identical as in (a); HPLC (Chiralcel® OD; 4% isopropanol/hexane): isomer (1S) 87,5%, isomer (1R) 12,5%, ee=75%; $[\alpha]_D=+17.3°$ (c=1, $CHCl_3$).

EXAMPLE 8

(S)-2-[(t-Butyl)dimethylsilyl]oxy-2-cyclopropylacetaldehyde (S)-1-[(t-Butyl)dimethylsilyl]oxy-1-cyklopropyl-2-(4-toluenesulfonyloxy)ethane (870 mg, 2.35 mmol) was dissolved in anhydrous dimethylsulfoxide (Aldrich, 15 mL). 2,4,6-Trimethylpyridine (1.25 ml, 1.14 g, 9.4 mmole) was added and the mixture was stirred under a nitrogen blanket. The flask containing the reaction mixture was placed in an oil bath heated at 150° C. The mixture was stirred/$N_2$ for another 2 hours, then cooled to room temperature, poured onto water (100 mL) and extracted with diisopropyl ether (60 mL). The phases were separated, the aqueous phase was re-extracted with diisopropyl ether (30 mL). The organic phases were combined and washed with 10% aqueous $KHCO_3$ (80 mL), then dried over anhydrous sodium sulfate (20 g), filtered and concentrated in vacuo. The crude product was purified on a silica gel column (230-400 mesh, 40 g, 15% $CH_2Cl_2$/hexane). This afforded a colorless oil (250 mg, 50%); $C_{11}H_{22}O_2Si$; $[\alpha]_D=(-)31$ (20° C., c=1, $CHCl_3$), lit. [M. J. Calverley *Synlett* 157, (1990)]: (−) 40.4; $^1$H-NMR (500 MHz, $CDCl_3$) δ 9.58 (1H, d: 2.2 Hz), 3.58 (1H, dd: 6.4, 2.2 Hz), 1.01 (1H, m), 0.91 (9H, s), 0.52 (2H, m), 0.43 (2H, m), 0.07 (3H, s) and 0.06 (3H,s) ppm.

EXAMPLE 9

(5Z,7E)-(1S,3R)-1,3-Bis[t-butyl(dimethylsilyl)oxy]-22-thio(2'-benzothiazolyl)-23,24-dinor-9,10-secochola-5,7, 10(19)-triene 2-Mercaptobenzothiazole (418 mg, 2.50 mmole) was placed in a 25 mL round bottom flask. With stirring, the mixture was cooled to 0° C., forming a suspension. Triphenylphosphine (655 mg, 2.50 mmole) was added in one portion, followed by a slow dropwise addition of a solution of (5Z,7E)-(1S,3R)-1,3-bis[t-butyl(dimethylosilyl)oxy]-22-hydroxy-23,24-dinor-9,10-secochola-5,7,10(19)-triene (960 mg, 1.67 mmole) in $CH_2Cl_2$ (4 mL). Immediately afterwards, a solution of diisopropyl azadicarboxylate (DIAD; 490 μL, 2.50 mmole) in $CH_2Cl_2$ (4 mL) was added. The mixture was stirred at 0° C. for another 1.5 h. Then the mixture was concentrated to dryness, toluene (2 mL) was added and the solution was applied to a column containing silica gel (5 g, 230-400 mesh) and eluted with 4% EtOAc/hexane. Pure fractions were pooled, concentrated and dried in vacuo to give (5Z,7E)-(1S,3R)-1,3-bis[t-butyl(dimethylosilyl)oxy]-22-thiobenzothiazol-23,24-dinor-9,10-secochola-5,7,10(19)-triene (1.10 g, 91%) as an off-white, amorphous solid; $UV_{ethanol}\lambda_{max}$ (300.4, 271.6, 246.0, 223.0); $^1$H-NMR δ 0.06 (12H, m), 0.57 (3H, s), 0.87 (18H, m), 1.15 (3H, d: 6.5 Hz), 3.07 (1H, m), 3.67 (1H, m), 4.19 (1H, m), 4.38 (1H, m), 4.87 (1H, bs), 5.19 (1H, bs), 6.04 (1H, d: 11.2 Hz), 6.24 (1H, d: 11.2 Hz), 7.27 (1H, m), 7.40 (1H, m), 7.74 (1H, m), 7.85 (1H, m) ppm.

EXAMPLE 10

(5Z,7E)-(1S,3R)-1,3-Bis[t-butyl(dimethylsilyl)oxy]-22-sulfonyl(2'-benzothiazolyl)-23,24-dinor-9,10-secochola-5,7,10(19)-triene (5Z,7E)-(1S,3R)-1,3-Bis[t-butyl(dimethylosilyl)oxy]-22-thio(2'-benzotiazolyl)-23,24-dinor-9,10-secochola-5,7,10(19)-triene (930 mg, 1.23 mmole) was dissolved in ethanol (6 ml). The solution was cooled to 0° C. A solution of ammonium heptamolybdenate hydrate (AHT; 350 mg, 0.283 mmol) in $H_2O_2$ (35%, 2 g, 20.6 mmole) was slowly added dropwise. The mixture was stirred for another 18 h at room temperature, then it was extracted with 10% aq. $Na_2SO_3$ (8 mL). The solvents were removed in vacuo, the residue was extracted with dichloromethane (2×10 mL). The organic phase was dried over anhydrous sodium sulfate, then concentrated. The residue was chromatographed on 230-400 mesh silica gel. The title compound was obtained as a white powder (600 mg, 62%); $UV_{ethanol}\lambda_{max}$ (268.2, 239.8, 215.0); $^1$H-NMR δ 0.05 (12H, m), 0.55 (3H, s), 0.88 (18H, m), 1.27 (3H, d: 6.5 Hz), 3.28 (1H, m), 3.65 (1H, m), 4.18 (1H, m), 4.36 (1H, m), 4.83 (1H, bs), 5.16 (1H, bs), 5.99 (1H, d: 11.2 Hz), 6.21 (1H, d: 11.2 Hz), 7.61 (2H, m), 8.02 (1H, m), 8.22 (1H, m) ppm.

EXAMPLE 11

(5Z,7E,22E)-(1S,3R,24S)-1,3,24-Trihydroxy-24-cyclopropyl-9,10-secochola-5,7,10(19),22-tetraene (Calcipotriol)

(5Z,7E)-(1S,3R)-1,3-Bis[t-butyl(dimethylsilyl)oxy]-22-sulfonyl(2'-benzothiazolyl)-23,24-dinor-9,10-secochola-5,7,10(19)-triene (356 mg, 0.492 mmole) was placed in a 5 mL round bottom flask and 1,2-dimethoxyethane (2 mL) was added. The solution was cooled to −70° C. and lithium bis(trimethylosilyl)amide solution (1 M in THF, 492 μL, 0.492 mmole) was added. The mixture was stirred for 30 min. at −70° C. (1S)-1-[t-Butyl(dimethyl)silyl]oxy-1-cyklopropylacetaldehyde (150 μL, 0.70 mmole) was slowly introduced. The mixture was stirred for 30 min. at −70° C., then at room temperature for 3. Brine (2 mL) was added and the mixture was extracted with hexane-ethyl acetate (1:4, 2×10 mL). The organic phase was dried over anhydrous sodium acetate (2 g). The solvents were removed in vacuo. The residue was dissolved in THF (2 mL), heated to 60° C., and treated with 1M tetrabutylammonium fluoride in THF (1.5 ml, 1.5 mmol), then stirred for 90 minutes. Brine (1 mL) was added, the phases were separated and the aqueous-brine phase was extracted with THF (3×5 mL). The organic phases were combined, dried over anhydrous sodium sulfate and concentrated. The residue was chromatographed on 230-400 mesh silica gel. This gave calcipotriol (60 mg, 31%); MS m/z 412 (M$^+$), 394, 376, 269, 251, 225, 197, 134(100%); HR MS $C_{27}H_{38}O_2$ Calc.: m/z M=394.2872, Found: M=394.2867; $UV_{ethanol}\lambda_{max}$ (264.8, 213.0); $^1$H-NMR δ 0.22 (1H, m), 0.32 (1H, m), 0.51 (2H, m), 0.57 (3H, s), 1.05 (3H, d: 6.6 Hz), 3.44 (1H, m), 4.23 (1H, bs), 4.43 (1H, bs), 5.00 (1H, bs), 5.32 (1H, bs), 5.47 (2H, m), 6.02 (1H, d: 11.2 Hz), 6.37 (1H, d: 11.2 Hz) ppm; $^{13}$C-NMR δ 1.83, 3.04, 12.27, 17.65, 20.49, 22.24, 23.54, 27.62, 29.05, 39.88, 40.35, 42.89, 45.28, 45.88, 56.07, 56.36, 66.86, 70.82, 76.99, 111.73, 117.11, 124.94, 128.98, 132.97, 137.96, 142.96, 147.67 ppm.

EXAMPLE 12

(5Z,7E,22E)-(1S,3R)-1,3-Dihydroxy-23-cyclopropyl-24-nor-9,10-secochola-5,7,10(19),22-tetraene (5Z,7E)-(1S,3R)-1,3-Bis[t-butyl(dimethylsilyl)oxy]-22-sulfonyl(2'-benzothiazol)-23,24-dinor-9,10-secochola-5,7,10(19)-triene (58 mg, 0.08 mmole) was placed in a 5 mL round bottom flask and 1,2-dimethoxyethane (0.4 ml) was added. The solution was cooled to −70° C. and lithium bis(trimethylsilyl)amide (1 M w THF, 80 μL, 0.08 mmole) was added dropwise. The mixture was stirred at −70° C. for 30 minutes, then cyclopropanecarboxaldehyde (11.6 μL, 0.16 mmol) was added. The mixture was stirred at −70° C. for 30 minutes, then at RT for 3 h. Brine (1 mL) was added and the mixture was extracted with hexane-EtOAc (1:4, 2×10 mL). The organic phases were combined, dried over $Na_2SO_4$ and concentrated in vacuo. The residue was dissolved in THF (1 mL), heated to 60° C. and treated with a TBAF solution (1M in THF, 0.5 ml, 0.5 mmol). The mixture was stirred for 1 h, then brine (2 mL) was added and the mixture was extracted with THF (3×5 mL). The organic phases were combined, dried over anhydrous $Na_2SO_4$, and the solvents were removed in vacuo. The residue was chromatographed on 230-400 mesh silica gel. This gave the title compound (15 mg, white, amorphous powder); $UV_{ethanol}\lambda max$ (265.4, 208.8); $^1$H-NMR δ 0.28 (2H, m), 0.54 (3H, s), 0.62 (2H, m), 1.01 (3H, d: 6.6 Hz), 4.24 (1H, m), 4.35 (1H, m), 4.90 (1H, dd: 15.2, 8.3 Hz), 5.00 (1H, bs), 5.32 (1H, bs), 5.34 (1H, dd: 15.2, 8.4 Hz), 6.01 (1H, d: 11.2 Hz), 6.37 (1H, d: 11.2 Hz) ppm.

EXAMPLE 13

(5Z,7E)-1,3-bis[t-Buthyl(dimethylsilyl)oxy]-22-thio(1'-phenyl-1'H-tetrazol-5'-yl)-23,24-dinor-9,10-secochola-5,7,10(19)-triene 1-Phenyltetrazol-5-thiol (558 mg, 3.14 mmole) was placed in a round bottom flask, methylene chloride (5 mL) was added and the mixture was cooled to 0° C. with stirring. Triphenylphosphine was added in an one portion (823 mg, 3.14 mmole). The resulted dispersion was stirred vigorously at 0° C. Independently, the solution of (5z,7E)-(1S,3R)-1,3-bis[t-butyl(dimethylsilyl)oxy]22-hydroksy-23,24-dinor-9,10-secochola-5,7,10(19)-triene (1.20 g, 2.09 mmole) in methylene chloride was prepared (5 mL). That solution was slowly added to the above prepared mixture of thiol and triphenylphosphine. Then diisopropyl-azadicarboxylate (DIAD; 634 mg, 3.14 mmole) was slowly added and stirring was continued at 0° C. for 1 h. After that the brine was added (2 mL) and the mixture was extracted with methylene chloride (2×10 mL). Organic layer was dried over anhydrous $Na_2SO_4$. After the solvent evaporation, the residue was dissolved in toluene (1 mL) and chromatographed on silica gel (230-400 mesh, 10 g). (5Z,7E)-1,3-Bis[t-butyl(dimethylsilyl)oxy]-22-thio(1'-phenyl-1'H-tetrazol-5'-yl)-23,24-dinor-9,10-secochola-5,7,10(19)-triene (1.15 g, 76%) was yielded as an off-white solid; UV $\lambda_{max}$ ($C_2H_5OH$) 251.6 nm; $^1$H-NMR δ: 0.07 (12H, bs, 2×SiMe$_2$), 0.56 (3H, s, 18-CH$_3$), 0.88 (18H, bs, 2 Si-tBu), 1.11 (3H, d: 6.2 Hz, 21-Me), 3.11 i 3.75 (2H, ddd: 12.4, 8.4, 2.9 Hz, 22-CH$_2$), 4.19 (1H, m, C(3)-H), 4.37 (1H, m, C(1)-H), 4.86 (1H, bs, 19Z-H), 5.19 (1H, bs, 19E-H), 6.02 (1H, d: 11.2 Hz, C(7)-H), 6.23 (1H, d: 11.2H, C(6)-H), 7.58 (5H, m, Ar—H).

EXAMPLE 14

(5Z,7E)-(1S,3R)-1,3-bis[t-Butyl(dimethylsilyl)oxy]-22-(1'-phenyl-1'H-tetrazol-5'-yl)sulfonyl-23,24-dinor-9,10-secochola-5,7,10(19)-triene (5Z,7E)-1,3-Bis[t-butyl(dimethylsilyl)oxy]-22-thio(1'-phenyl-1'H-tetrazol-5'-yl)-23,24-dinor-9,10-secochola-5,7,10(19)-triene (776 mg, 1.06 mmole) and powdered molecular sieves 4A (500 mg) were placed in a round bottom flask after which acetonitrile was added (25 mL). The mixture was stirring for 5 min. and then tetrapropylammonium perrutenate (TPAP, 15 mg, 0.04 mmole) was added. The mixture was stirred for further 5 h at 50° C. The solvents were distilled under reduced pressure, the residue was dissolved in toluene (2 mL) and chromatographed on silica gel (230-400 mesh, 50 g). Unreacted sulfide was recovered (244 mg) and (5Z,7E)-(1S,3R)-1,3-bis[t-butyl(dimethylsilyl)oxy]-22-(1'-phenyl-1'H-tetrazol-5'-yl)sulfonyl-23,24-dinor-9,10-secochola-5,7,10(19)-triene (70 mg, 13%) as an off-white powder: UV $\lambda_{max}$, ($C_2H_5OH$) 250.6 nm; MS m/z 766 (M$^+$, 11), 738 (7), 709 (5), 634 (47), 606 (20), 248 (100); $^1$H-NMR δ: 0.07 (12H, bs, 2×SiMe$_2$), 0.58 (3H, s, 18-Me), 0.88 (18H, bs, 2×t-BuSi), 1.26 (3H, d: 6.4 Hz, 21-Me), 3.51 i 3.92 (2H, ddd: 14.3, 9.9, 1.5 Hz, 22-CH$_2$), 4.19 (1H, m, C(3)-H), 4.37 (1H, m, C(1)-H), 4.85 (1H, bs, 19Z-H), 5.19 (1H, bs, 19E-H), 6.01 (1H, d: 11.3 Hz, C(7)-H), 6.22 (1H, d: 11.3 Hz, C(6)-H), 7.61 (5H, m, Ar—H) ppm.

EXAMPLE 15

(5Z,7E,22E)-(1S,3R,24S)-1,3,24-Trihydroxy-24-cyclopropyl-9,10-secochola-5,7,10(19),22-tetraene (Calcypotriol)

(5Z,7E)-(1S,3R)-1,3-bis[t-Butyl(dimethylsilyl)oxy]-22-(1'-phenyl-1'H-tetrazol-5'-yl)sulfonyl-23,24-dinor-9,10-secochola-5,7,10(19)-triene (60 mg, 0.08 mmole) and 1,2-dimethoxyethane (0.8 ml) were placed in a 5 ml round bottom flask. The resulted solution was cooled to −70° C. and then 1M solution lithium bis(trimethylsilyl)amidate in THF was added (80 μL, 0.08 mmole). The mixture was stirred for 30 min. at −70° C., then (1S)-1-[t-butyl(dimethyl)]silyloxy-1-cyclopropylacetaldehyde was added (40 ml, 0.19 mmole). The mixture was stirred at −70° C. for further 30 min. and then at room temp. for 3 h. Brine was added (1 mL) and the mixture was extracted with the mixture hexane-ethyl acetate (1:4, 2×10 mL). Organic layer was dried over anhydrous Na$_2$SO$_4$, and then the solvents were evacuated in vacuo. The residue was chromatographed on silica gel (230-400 mesh, 5 g). (5Z,7E,22E)-(1S,3R,24S)-1,3,24-Trihydroxy-24-cyclopropyl-9,10-secochola-5,7,10(19),22-tetraene (11.0 mg, 34%) yielded: HPLC analysis and the $^1$H-NMR spectra identical as in Example 4.

What is claimed is:
1. A process for the preparation of compounds of Formula 1

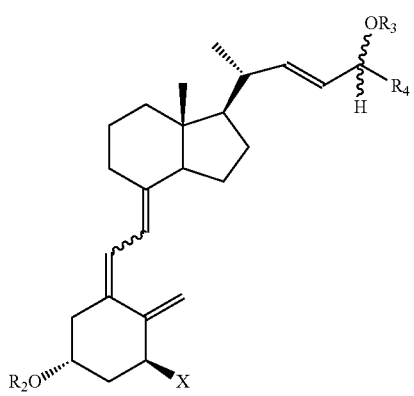

having a (5Z) configuration, wherein X represents a hydrogen atom, a hydroxy group or an OR$_1$ group, where R$_1$, R$_2$ and R$_3$ may be the same or different and represent groups suitable for hydroxyl protection, and R$_4$ is a C$_{1-6}$ alkyl chain or a C$_{3-6}$ cycloalkyl group, optionally substituted with C$_{1-3}$ alkyl groups, comprising the steps of:
(a) reacting a sulfone of Formula 5, possessing a (5E) or (5Z) configuration, wherein X represents a hydrogen atom, a hydroxyl group or an OR$_1$ group, where R$_1$ and R$_2$ may be the same or different and represent groups suitable for hydroxyl protection-and R$_5$ is a heterocyclic group comprising at least one heteroatom selected from among oxygen, nitrogen, phosphorus and sulfur,

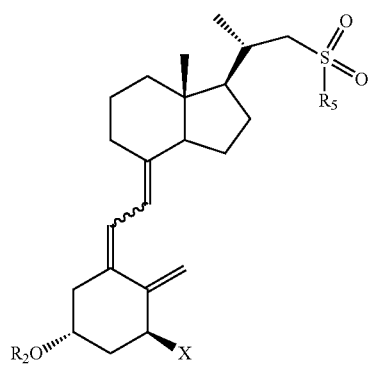

with an aldehyde of Formula 6, having an (R) or an (S) configuration at the carbon atom directly attached to the carbonyl group, wherein R$_3$ is a hydrogen atom or a group suitable for hydroxyl protection and R$_4$ is a C1-6 alkyl chain or a C3-6 cycloalkyl group, optionally substituted with C1-3 alkyl groups,

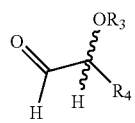

in the presence of a strong base, in a solvent selected from the group consisting of hydrocarbons and ethers, and
(b) optionally, in case the product obtained in step (a) represented by formula 1 in which R$_1$, R$_2$, and R$_3$ are the same or different and represent groups suitable for hydroxyl protection, and R$_4$, is a C$_{1-6}$ alkyl chain or a C$_{3-6}$ cycloalkyl group, optionally substituted with C$_{1-3}$ alkyl groups, has a (5E) configuration, it is subjected to photoisomerization reaction to a compound represented by formula 1 in which R$_1$, R$_2$, and R$_3$ are the same or different and represent groups suitable for hydroxyl protection, and R$_4$ is a C$_{1-6}$ alkyl chain or a C$_{3-6}$ cycloalkyl group, optionally substituted with C$_{1-3}$ alkyl groups, having a (5Z) configuration, and
(c) removing the protective groups, R$_1$, R$_2$ and R$_3$ simultaneously or one after another, from the compound of formula 1 to obtain the compound of formula 1 in which X represents a hydrogen atom or R$_1$ group and R$_1$, R$_2$ and R$_3$ represent a hydrogen atom.
2. A process according to claim 1 wherein the base is a strong organic base selected from a group consisting of lithium N,N-bis(trimethylsilyl)amide, sodium N,N-bis(trimethylsilyl)amide and potassium N,N-bis(trimethylsilyl)amide.

3. A process according to claim 1 wherein the aprotic solvent is selected from a group comprising hydrocarbons and ethers, preferably is 1,2-dimethoxyethane and tetrahydrofuran.

4. A process according to claim 1 wherein the sulfone of Formula 5, possessing a (5E) or (5Z) configuration, in which X is the $OR_1$ group and $R_1$, $R_2$ and $R_3$ are hydrogen atoms, or R1, R2 and R3 are the same or different and represent groups suitable for hydroxyl protection and $R_5$ is an aryl group or a heterocyclic group, is reacted with an aldehyde of Formula 6, where $R_3$ is a hydrogen atom or a protective group to obtain calcipotriol.

5. The process according to claim 4 wherein the sulfone of Formula 5 is reacted with (s)-2-[(t-butyl)dimethylsilyl]oxy-2-cyclopropylacetaldehyde.

6. The process according to claim 1 wherein calcipotriol is obtained.

* * * * *